(12) United States Patent
Shao et al.

(10) Patent No.: US 11,099,163 B2
(45) Date of Patent: Aug. 24, 2021

(54) SYSTEM AND METHOD FOR CALIBRATION OF VOLATILE ORGANIC COMPOUND DETECTING INSTRUMENTS

(71) Applicant: Honeywell International Inc., Morris Plains, NJ (US)

(72) Inventors: Chunyu Shao, Shanghai (CN); Nico Xu, Shanghai (CN); Kevin Chen, Shanghai (CN); Sam Su, Shanghai (CN); Yong Chen, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 126 days.

(21) Appl. No.: 16/392,450

(22) Filed: Apr. 23, 2019

(65) Prior Publication Data

US 2019/0250133 A1 Aug. 15, 2019

Related U.S. Application Data

(63) Continuation of application No. 15/184,388, filed on Jun. 16, 2016, now Pat. No. 10,295,515.

(51) Int. Cl.
*G01N 33/00* (2006.01)

(52) U.S. Cl.
CPC ..... *G01N 33/0006* (2013.01); *G01N 33/0047* (2013.01)

(58) Field of Classification Search
CPC ................ G01N 33/0006; G01N 33/0047
See application file for complete search history.

(56) References Cited

U.S. PATENT DOCUMENTS

| 3,427,862 A | 2/1969 | Hubner |
| 3,854,319 A | 12/1974 | Burroughs |
| 4,063,821 A | 12/1977 | King |
| 4,332,771 A | 6/1982 | Leichnitz |

(Continued)

FOREIGN PATENT DOCUMENTS

| CN | 102460028 A | 5/2012 |
| CN | 104833622 A | 8/2015 |

(Continued)

OTHER PUBLICATIONS

Europe Patent Application No. 17175870.9, partial European search report, dated Sep. 21, 2017, 11 pages.

(Continued)

*Primary Examiner* — Natalie Huls
(74) *Attorney, Agent, or Firm* — Alston & Bird LLP

(57) ABSTRACT

Embodiments relate generally to systems and methods for calibrating a gas detector. Some embodiments may include a gas detector comprising one or more sensing elements operable to detect volatile organic compounds (VOC), and a probe operable to provide air flow into the gas detector, wherein the probe comprises: a housing operable to attach to a main body of the gas detector and operable to hold a calibration tube during calibration of the gas detector; a cap operable to attach to the housing and operable to fit over and cover the calibration tube; and one or more inlets, wherein when a calibration tube is inserted into the probe, the air flows through the calibration tube. In some embodiments of the gas detector, the calibration tube inserted into the probe comprises activated carbon fiber (ACF) filter material.

19 Claims, 4 Drawing Sheets

(56) References Cited

U.S. PATENT DOCUMENTS

| | | |
|---|---|---|
| 4,388,272 A | 6/1983 | Gesteland |
| 4,389,372 A | 6/1983 | Lalin |
| 5,138,869 A | 8/1992 | Tom |
| 5,462,908 A * | 10/1995 | Liang .................... B01D 53/02 502/401 |
| 5,479,815 A | 1/1996 | White |
| 2004/0146432 A1 | 7/2004 | Loomis |
| 2006/0118416 A1 | 6/2006 | Liu et al. |
| 2010/0095843 A1 | 4/2010 | Gebert |
| 2010/0104473 A1 | 4/2010 | Kirollos |
| 2012/0063956 A1 | 3/2012 | Truex |
| 2012/0091220 A1 | 4/2012 | Chand |
| 2013/0171687 A1 | 7/2013 | Moularat et al. |
| 2016/0258874 A1 | 9/2016 | Truex |
| 2017/0363595 A1 | 12/2017 | Shao et al. |

FOREIGN PATENT DOCUMENTS

| | | |
|---|---|---|
| CN | 104995511 A | 10/2015 |
| CN | 105510528 A | 4/2016 |
| CN | 107525886 A | 12/2017 |
| EP | 3258261 A | 12/2017 |

OTHER PUBLICATIONS

Europe Patent Application No. 17175870.9, Extended European search report, dated Jan. 12, 2018, 9 pages.
U.S. Appl. No. 15/184,388, Restriction Requirement, dated Feb. 27, 2018, pages.
U.S. Appl. No. 15/184,388, Office Action, dated Jul. 20, 2018, 17 pages.
U.S. Appl. No. 15/184,388, Notice of Allowance dated Jan. 4, 2019, 10 pages.
Annex to the communication dated Aug. 6, 2020 for EP Application No. 17175870.
Communication from the Examining Division dated Aug. 6, 2020 for EP Application No. 17175870.
CN Office Action, including Search Report, dated Apr. 19, 2021 for CN Application No. 201710450789, 12 pages.
Communication about intention to grant a European patent dated Apr. 28, 2021 for EP Application No. 17175870, 5 pages.
English Translation of CN Office Action dated Apr. 19, 2021 for CN Application No. 201710450789, 11 pages.
Lai, Cai. "Properties and Applications of Activated Carbon Fiber in Air Cleaner." Pollution Control Technology (2003):36-39. Abstract only retreived from the Internet at <https://www.semanticscholar.org/paper/Properties-and-Applications-of-Activated-Carbon-in-Lai/7fcf8e2d3e144d61df28778f44afaa073780cb6a#paper-header> on Jun. 21, 2021.

* cited by examiner

SYSTEM AND METHOD FOR CALIBRATION OF VOLATILE ORGANIC COMPOUND DETECTING INSTRUMENTS

CROSS-REFERENCE TO RELATED APPLICATIONS

This is a continuation application of U.S. patent application Ser. No. 15/184,388, filed Jun. 16, 2016 and entitled "System and Method for Calibration of Volatile Organic Compound Detecting Instruments" by Chunyu Shao et al. which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detectors may be carried by workers and/or located throughout a work place and may detect gases in the environment. Gas detectors may be operable to alert a user and/or supervisor when a harmful gas or level of gas is detected. To ensure that gas detectors are functioning properly, the detectors may be periodically calibrated (or zeroed). Some calibration methods may involve providing purified or filtered air to the gas detector and calibrating the resulting readings to a zero reference point.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
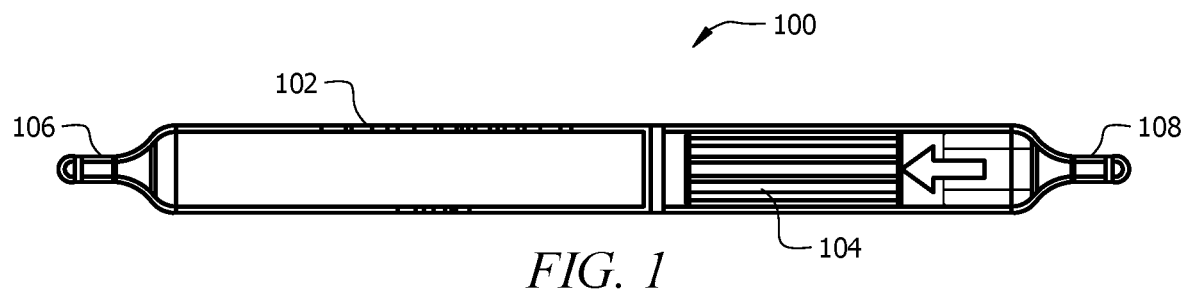
FIG. 1 illustrates a calibration tube according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for calibrating a gas detector. Some gas detectors may be operable to detect volatile organic compounds (VOCs). Indoor and outdoor VOCs endanger human health, and increases of VOC concentration in production environments may decrease product quality and yield. To ensure safety and efficiency, it is important to quickly and accurately detect trace amounts of total VOC (TVOC) concentration levels (such as in parts per million (ppm) and/or parts per billion (ppb)). A photoionization detector (PID) (which may also be referred to more generally as a "gas detector") may be typically used for TVOC detection, and may be characterized by high sensitivity (achieving ppb level resolution), quick response time (generally a few seconds), and a wide range of detectable substances (the majority of VOCs can be detected by PID). However, there are some issues in current PID rapid detection. PIDs need to be regularly zero-calibrated because of the tendency for zero drift in the sensor. Alternatives to zero calibration include using cylinder clean air and/or using a filter, but both of these solutions have disadvantages. When using cylinder clean air, it may be troublesome to prepare and preserve very pure air, and it may be inconvenient and high cost.

When using a filter during calibration, activated carbon may be used as adsorbent to make the VOC zeroing tube. The filter purifies ambient air for zero calibration and provides a zero standard, and may be low cost and easy to use. However, typical calibration tubes having activated carbon filters not only remove VOC from the ambient air, but also remove water vapor. This causes the humidity of the calibration gas to be different from the humidity of the sample gas, which may affect the accuracy of the readings of the PID. For some rapid detection means, such as PID, water vapor will affect the response. Therefore, the humidity difference between filtered calibration gas and sample gas will lead to reading deviation.

Disclosed embodiments may comprise systems and methods for humidifying the filter material in a calibration tube for use with a PID. The calibration filter material may be pretreated to maintain the humidity levels of the ambient air.

The absorbent material for the calibration tube may comprise a porous material with a large specific surface area, and the material may not be strongly polar or absolutely non-polar (where strongly polar materials may absorb too much water from the filtered gas, and non-polar materials cannot absorb polar VOC). Additionally, the material may be intrinsically stable, operable to quickly absorb VOC gas and not release the absorbed VOCs.

In some embodiments of the calibration tube, the filter material may comprise activated carbon fibers (ACF), which may have high adsorbing efficiency and quick humidity equilibrium speed due to the unique mesh fabric structure and micro-pores of the material, compared with granular activated carbon. The ACF is designed to quickly generate relatively pure gas by a special pretreatment method as described herein. Embodiments of the calibration tube may comprise activated carbon fiber as adsorbent material, where the ACF may be pretreated, thereby humidifying the adsorbent.

In some embodiments, the humidity of the gas entering the PID may be maintained by the calibration tube at approximately 50% relative humidity (RH). In other embodiments, the humidity may be maintained by the calibration tube at any point between approximately 10-90% RH depending on the use and application of the calibration tube.

Referring now to FIG. 1, an exemplary embodiment of a calibration tube 100 is shown. The calibration tube 100 may comprise a glass casing 102, wherein a portion of the glass casing 102 may be broken before the tube 100 is used. In an embodiment, the calibration tube 100 may comprise a filter material 104, wherein the calibration tube 100 may be operable to filter ambient air to generate a zero standard for calibrating a gas detector. In some embodiments, the filter material 104 may comprise ACF (as described above). In some embodiments of the calibration tube 100, the ACF filter material 104 may be pretreated to enable the filter material to maintain a humidity level greater than zero, and near the ambient humidity level. The calibration tube 100 may comprise a first end 106 and a second end 108. The ends 106 and 108 of the calibration tube may be broken prior to use of the tube, to allow air to flow into the calibration tube 100 and then into the gas detector (or PID) to calibrate the gas detector.

Figure 2B:
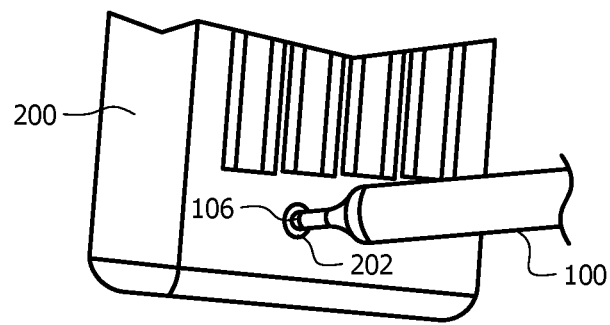
FIGS. 2A-2B illustrate a calibration tube and packaging according to an embodiment of the disclosure.
Figure 2A:
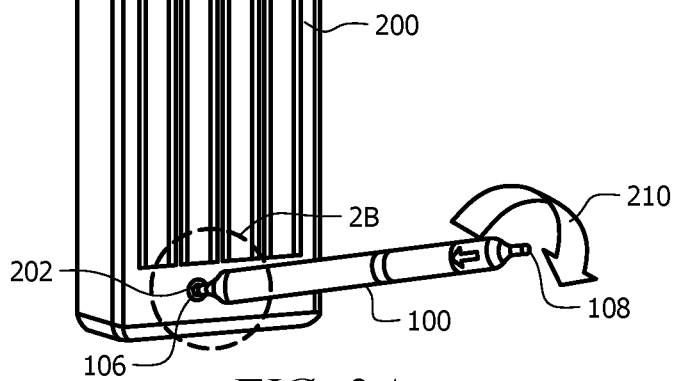

FIGS. 2A-2B illustrate a method of breaking a portion of the calibration tube 100 (such as one or more of the ends 106 and 108). The calibration tube 100 may be packaged with other tubes in a package box 200, where the tubes may be delivered to users in these boxes 200. In an embodiment, the box 200 may comprise a "tube tip breaker" 202 located on the exterior of the box 200. The tube tip breaker 202 may comprise a metal ring, hole, or other similar material operable to break the glass material of the tube 100. The tube 100 may be inserted by a user into the tube tip breaker 202 and twisted, turned, and/or bent by the user (such as in the direction indicated by arrow 210). The first end 106 of the tube 100 that is inserted into the tube tip breaker 202 may be broken, allowing air flow into and/or out of the calibration tube 100. FIG. 2B illustrates a closer view of the tube tip breaker 202. In some embodiments, both ends 106 and 108 of the tube 100 may be broken using this method before the calibration tube is used with a gas detector.

Figure 3:
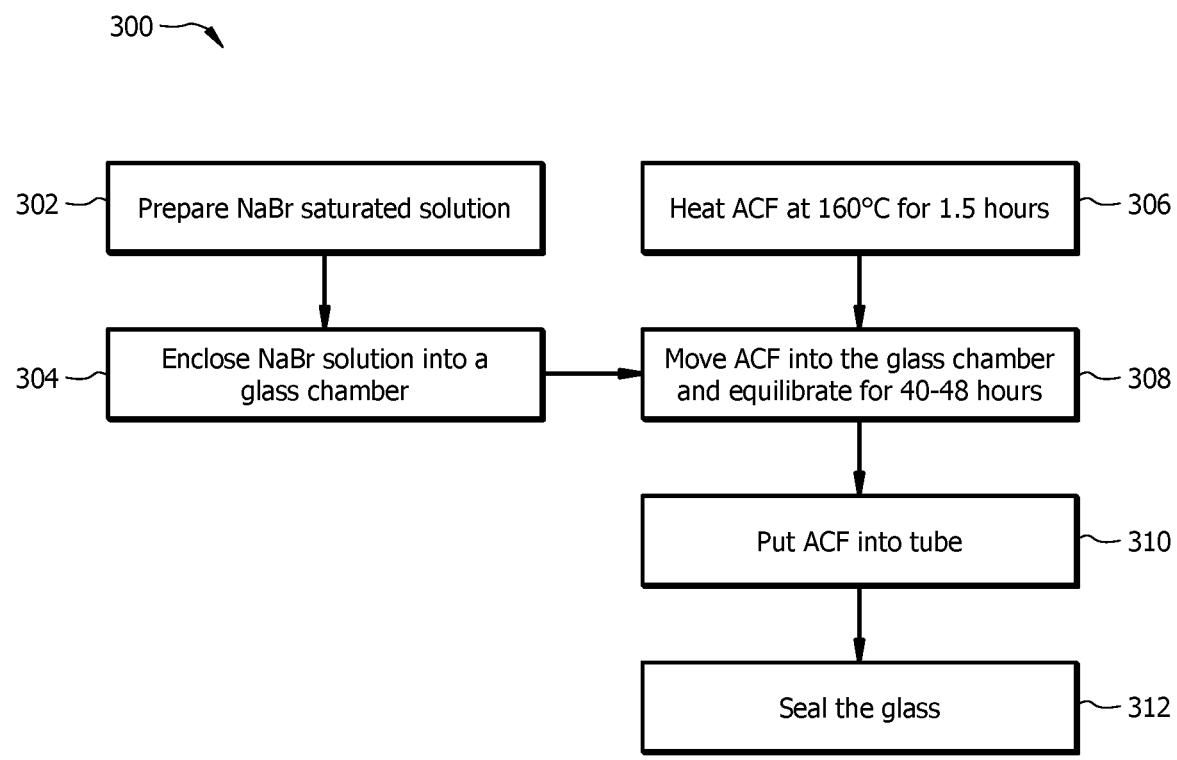
FIG. 3 illustrates a method according to an embodiment of the disclosure.

Referring to FIG. 3, a method 300 for assembling the calibration tube (described above) is shown. At step 302, a pretreatment saturated solution of sodium bromide (NaBr) may be prepared. In some embodiments, the NaBr solution may be made up as a slushy mixture with distilled water and chemical pure salt. At step 304, the NaBr solution may be enclosed in a sealed clean glass chamber, keeping the surface area of the solution as large as possible. At step 306, ACF may be desorbed in an oven at approximately 160° C. and kept heated at that temperature for approximately 1.5 hrs. At step 308, the heated ACF may be moved into the glass chamber containing the NaBr solution, wherein the glass chamber may be sealed. The ACF and NaBr solution mixture may be allowed to equilibrate humidity for approximately 40 to 48 hours. In some embodiments, ACF and NaBr solution mixture may be allowed to equilibrate for at least 24 hours. Then, at step 310, the ACF that has been pretreated with the NaBr solution may be placed in a glass calibration tube, which at step 312, may be immediately sealed.

To complete calibration of a gas detector (such as a PID) using a calibration tube, the two ends of the glass calibration tube may be broken (as described above), and the calibration tube may be inserted into the air flow entering the gas detector. In some embodiments, the gas detector may comprise a probe that provides air flow to the sensor elements of the gas detector. Typically, an adapter may be used to attach a calibration tube to the probe, such that air entering the probe first passes through the calibration tube. However, the process of attaching the tube may be complicated, requiring multiple separate elements, and one end of the broken glass tube is exposed, creating the potential for cutting of a user's hands by accident while completing the calibration.

Embodiments of the disclosure include a probe structure that allows for an efficient and safer calibration process using a glass calibration tube.

Figure 4:
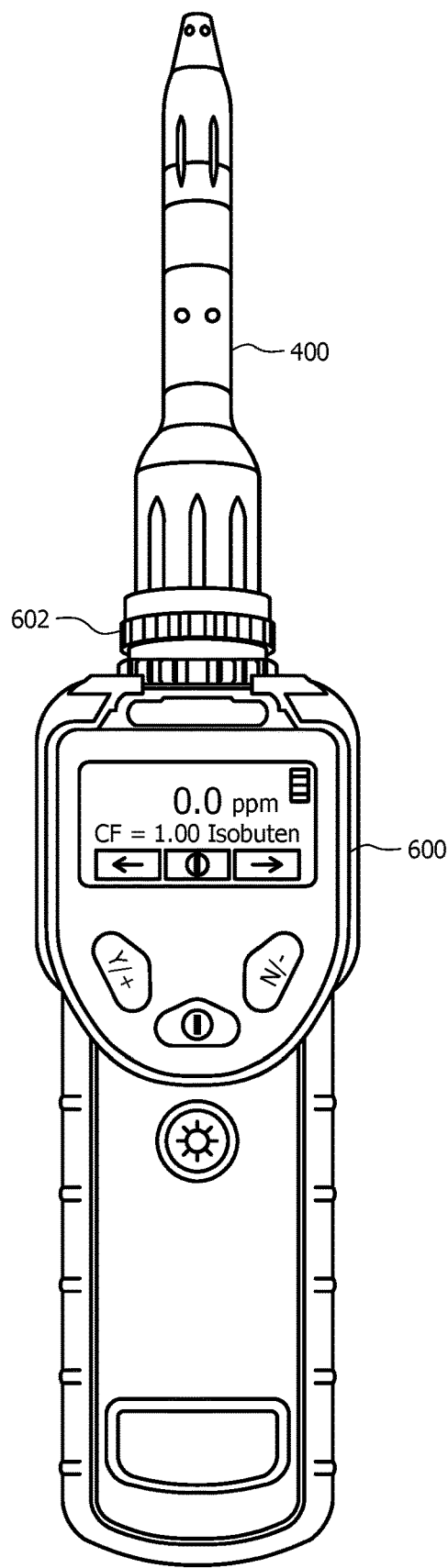
FIG. 4 illustrates a gas detector according to an embodiment of the disclosure.

FIG. 4 illustrates an exemplary embodiment of a gas detector 600 where the gas detector 600 comprises a probe section 400. During normal use, the gas that is sensed by the gas detector 600 may enter the gas detector 600 via the probe 400. In the embodiment shown, the probe 400 may comprise an elongated, thin component extending from the main body of the gas detector 600. Typically, to calibrate the gas detector 600, a calibration tube (such as the calibration tube 100 described above) may be coupled to the probe 400 in some way, such that the gas sensed by the gas detector 600 is filtered by the calibration tube and/or is received only from the calibration tube.

Figure 5:
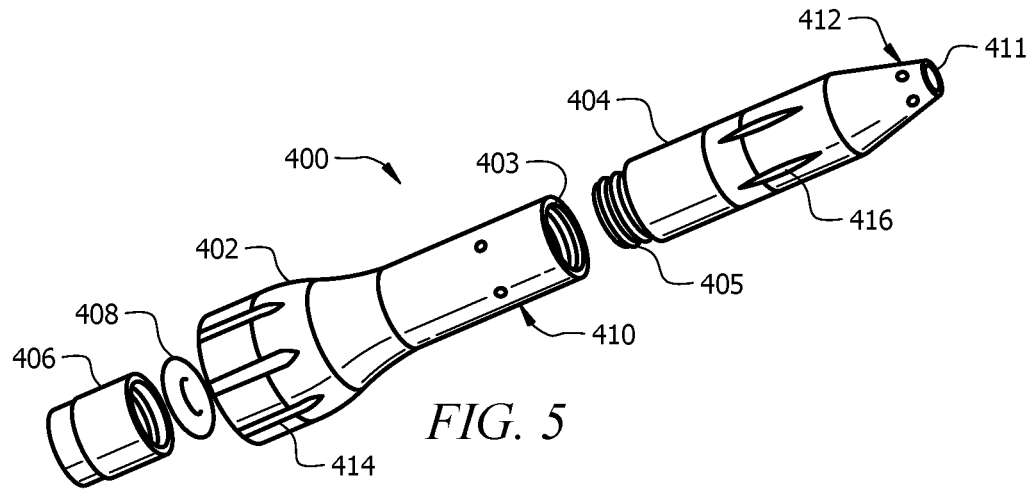
FIG. 5 illustrates a probe according to an embodiment of the disclosure.

FIG. 5 illustrates an exemplary embodiment of a probe 400, wherein the probe 400 is operable to attach to a gas detector (such as the gas detector 600 described above). The probe 400 may comprise a housing 402 and cap 404, wherein the housing 402 may be operable to attach to a gas detector, and the cap 404 may be operable to thread onto and off of the housing 402 via threads 403 and 405. In some embodiments, the cap 404 and housing 402 may attach via another attachment means, such as a clip, adhesive, a snap mechanism, etc. The attachment between the housing 402 and cap 404 may allow for easy and efficient removal and reattachment of the cap 404 to/from the housing 402. In some embodiments, the housing 402 and/or cap 404 may comprise grooves 414 and 416 (or another gripping feature) providing a secure gripping surface for the user.

The probe 400 may comprise an inlet 411 near the top of the probe 400. In some embodiments, the probe 400 may comprise secondary inlets 412 and 410 located on at least one of the housing 402 and/or the cap 404, operable to let gas into the probe 400, particularly if something is blocking the top inlet 411 of the probe 400. In some embodiments, the housing 402 may comprise inlets 410, and the cap 404 may comprise inlets 412. In some embodiments, only the cap 404 may comprise inlets 412. In some embodiments of the probe 400, the housing 402 may attach to the gas detector, and the probe 400 may comprise an O-ring 408 and/or support block 406 located at the attachment with the gas detector. In some embodiments, the support block 406 may comprise a PTFE material. In some embodiments, the O-ring 408 may be operable to seal against the end of a calibration tube that is inserted into the housing 402.

Figure 6:
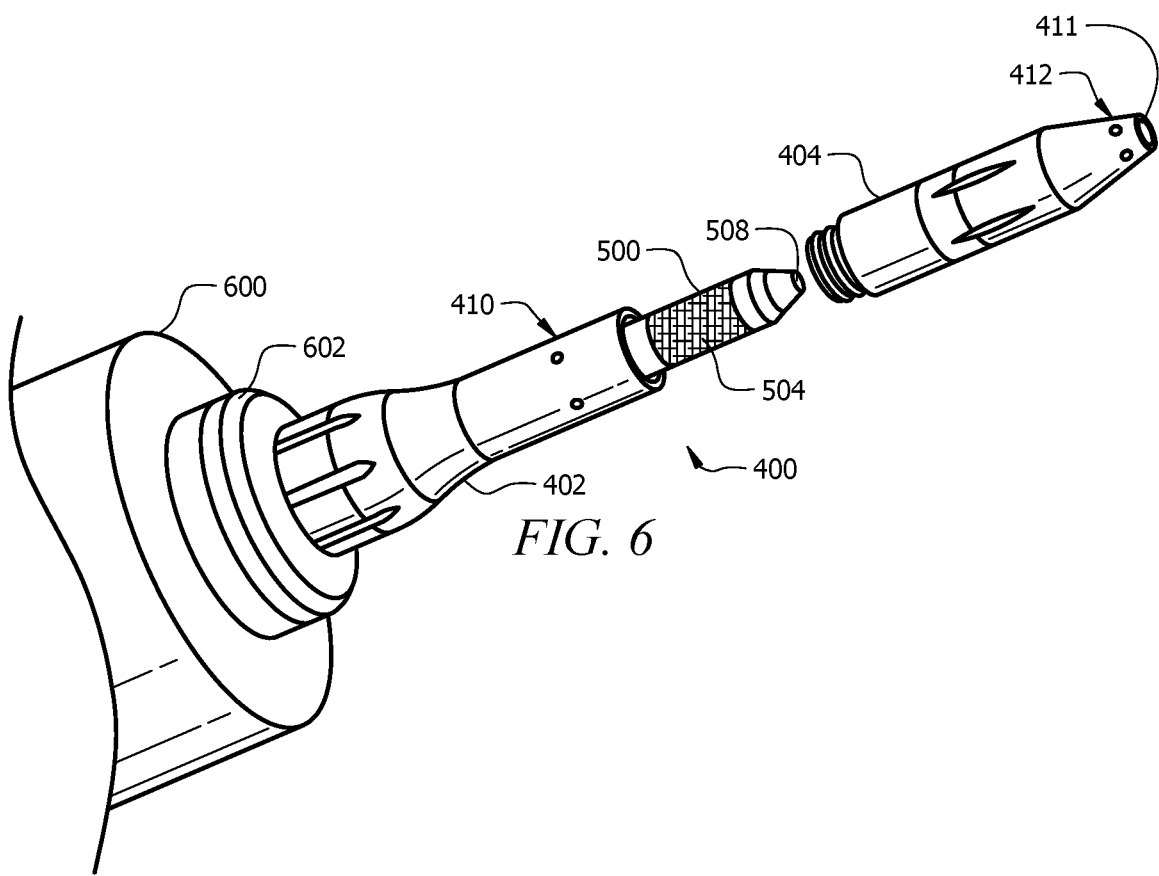
FIG. 6 illustrates the probe of FIG. 5 attached to a gas detector according to an embodiment of the disclosure.

FIG. 6 illustrates another view of the probe 400 attached to a gas detector 600 via the connection point 602. In the embodiment shown in FIG. 6, a calibration tube 500 (similar to calibration tube 100 shown in FIG. 1) may be inserted directly into the housing 402 of the probe 400. In some embodiments, the ends (or tips) 508 of the calibration tube 500 may be broken before the calibration tube 500 is inserted into the probe 400, such that the air flow into the gas detector 600 may pass through the calibration tube 500. To secure the probe 400, and also to protect a user from the broken glass ends 508 of the tube, the cap 404 may be attached over the calibration tube 500 to the housing 402, covering the tube 500. Then, calibration of the gas detector 600 may be completed, and the calibration tube 500 may be held securely and safely within the probe 400. In some embodiments, the calibration tube 500 may comprise a filter material 504 (similar to the filter material 104 described above).

When calibration is completed, the calibration tube 500 may be removed from the probe, the cap 404 may be reattached to the housing 402, and normal detection by the gas detector 600 may proceed. In an alternative embodiment, the normal detection by the gas detector 600 may proceed with only the housing 402 attached to the gas detector 600. In another embodiment, the probe 400 may comprise a "calibration" cap used during calibration and a "detection" cap used during normal detection that provide different functionality for the probe 400 depending on the use.

Some embodiments of the disclosure may comprise a gas detector comprising one or more sensing elements operable to detect volatile organic compounds (VOC) and a probe operable to provide air flow into the gas detector, wherein the probe comprises: a housing operable to attach to a main body of the gas detector and operable to hold a calibration tube during calibration of the gas detector; a cap operable to attach to the housing and operable to fit over and cover the calibration tube; and one or more inlets, wherein when a calibration tube is inserted into the probe, the air flows through the calibration tube.

In an embodiment of the gas detector, the calibration tube inserted into the probe comprises activated carbon fiber (ACF) filter material. In an embodiment of the gas detector, the calibration tube inserted into the probe comprises ACF filter material that has been pretreated with a sodium bromide (NaBr) solution. In an embodiment of the gas detector, the calibration tube inserted into the probe comprises broken glass ends, allowing air flow into and out of the calibration tube. In an embodiment of the gas detector, the probe further comprises threads between the housing and the cap. In an embodiment of the gas detector, the probe further comprises gripping elements on the exterior of at least one of the housing and cap. In an embodiment of the gas detector, the probe further comprises an O-ring operable to seal with one end of the calibration tube when it is inserted into the housing. In an embodiment of the gas detector, the probe further comprises air inlets on the housing. In an embodiment of the gas detector, the probe further comprises air inlets on the cap. In an embodiment of the gas detector, the probe further comprises a support block operable to seal the probe with the gas detector.

Some embodiments of the disclosure may comprise a method for completing a calibration process for a gas detector comprising providing a gas detector comprising a probe, wherein the probe comprises a housing operable to attach to a main body of the gas detector and operable to hold a calibration tube during calibration of the gas detector; a cap operable to attach to the housing and operable to fit over and cover the calibration tube; and one or more inlets, wherein when the calibration tube is inserted into the probe, the air flows through the calibration tube; breaking a portion of the calibration tube to allow air flow through the calibration tube; inserting the calibration tube into the housing of the probe; attaching the cap of the probe onto the housing, wherein the cap covers the calibration tube; completing calibration of the gas detector while the calibration tube is inserted into the probe; removing the calibration tube from the probe; and receiving gas readings by the gas detector.

In an embodiment of the method, the method may further comprise providing an activated carbon fiber (ACF) filter material; pretreating the ACF filter material with a sodium bromide (NaBr) solution; placing the ACF filter material into the calibration tube; and sealing the calibration tube. In an embodiment of the method, pretreating the ACF filter material comprises heating the ACF to 160° C. for approximately 1.5 hours; enclosing the ACF filter material in a glass chamber with a NaBr solution; and allowing the ACF filter material and NaBr solution to equilibrate for at least 24 hours. In an embodiment of the method, the gas detector is operable to detect volatile organic compounds (VOC). In an embodiment of the method, breaking a portion of the calibration tube comprises breaking a first tip on one end of the tube; and breaking a second tip on the other end of the tube. In an embodiment of the method, attaching the cap of the calibration tube onto the housing comprises threading the cap onto the housing.

Some embodiments of the disclosure may comprise a method for manufacturing a calibration tube for use with a gas detector comprising providing an activated carbon fiber (ACF) filter material; pretreating the ACF filter material with a sodium bromide (NaBr) solution; placing the ACF filter material into the calibration tube; and sealing the calibration tube.

In an embodiment of the method, pretreating the ACF filter material comprises heating the ACF to 160° C. for approximately 1.5 hours, enclosing the ACF filter material in a glass chamber with a NaBr solution, and allowing the ACF filter material and NaBr solution to equilibrate for at least 24 hours. In an embodiment of the method, the method may further comprise breaking a portion of the calibration tube to allow air flow through the calibration tube; inserting the calibration tube into a first portion of a probe attached to the gas detector; attaching a second portion of the probe onto the first portion, wherein the second portion covers the calibration tube; and completing calibration of the gas detector while the calibration tube is inserted into the probe. In an embodiment of the method, the method may further comprise employing the gas detector to detect volatile organic compounds (VOC).

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detector comprising:
   one or more sensing elements operable to detect volatile organic compounds (VOC); and
   a probe operable to provide air flow into the gas detector, wherein the probe comprises:
      a housing operable to attach to a main body of the gas detector, and operable to hold a calibration tube during calibration of the gas detector;
      a cap operable to attach to the housing, and operable to fit over and cover the calibration tube; and
      one or more inlets, wherein when the calibration tube is inserted into the probe, the air flow is through the calibration tube, wherein the calibration tube inserted into the probe comprises activated carbon fiber (ACF) filter material, wherein the ACF filter material is pretreated by a method comprising:
         heating the ACF filter material to 160° C. for approximately 1.5 hours;
         enclosing the ACF filter material in a glass chamber with a salt bath solution; and
         allowing the ACF filter material and the salt bath solution to equilibrate for at least 24 hours.

2. The gas detector of claim 1, wherein the calibration tube inserted into the probe comprises the ACF filter material which has been pretreated with a sodium bromide (NaBr) solution.

3. The gas detector of claim 1, wherein the calibration tube inserted into the probe comprises broken glass ends, and wherein the broken glass ends allow an air flow into and out of the calibration tube.

4. The gas detector of claim 1, wherein the probe further comprises threads between the housing and the cap.

5. The gas detector of claim 1, wherein the probe further comprises gripping elements on an exterior of at least one of the housing and the cap.

6. The gas detector of claim 1, wherein the probe further comprises an O-ring operable to seal with one end of the calibration tube when it is inserted into the housing.

7. The gas detector of claim 1, wherein the probe further comprises air inlets on the housing.

8. The gas detector of claim 1, wherein the probe further comprises air inlets on the cap.

9. A calibration device comprising:
   a housing operable to attach to a main body of a gas detector, and operable to hold a calibration tube during calibration;
   a cap operable to attach to the housing, and operable to fit over and cover the calibration tube; and
   one or more inlets, wherein when the calibration tube is inserted into the calibration device, an air flows through the calibration tube, and wherein the calibration tube comprises activated carbon fiber (ACF) filter material pretreated to enable the ACF filter material to maintain a humidity level greater than zero, wherein the ACF filter material is retreated by a method comprising:
      heating the ACF filter material to 160° C. for approximately 1.5 hours;
      enclosing the ACF filter material in a glass chamber with a salt bath solution; and
      allowing the ACF filter material and the salt bath solution to equilibrate for at least 24 hours.

10. The calibration device of claim 9, wherein the gas detector is operable to detect volatile organic compounds (VOC).

11. The calibration device of claim 9, wherein the salt bath solution comprises an alkali metal halide solution, potassium carbonate, magnesium nitrate, or potassium sulfate.

12. The calibration device of claim 9, wherein the calibration tube further comprises a first tip on one end of the calibration tube and a second tip on another end of the calibration tube, wherein the first tip and the second tip are broken during the calibration of the gas detector.

13. A method for manufacturing a calibration tube for use with a gas detector comprising:
   providing an activated carbon fiber (ACF) filter material;
   pretreating the ACF filter material to enable the ACF filter material to maintain a humidity level greater than zero, wherein pretreating the ACF filter material comprises:
      heating the ACF filter material to 160° C. for approximately 1.5 hours;
      enclosing the ACF filter material in a glass chamber with a salt bath solution; and
      allowing the ACF filter material and the salt bath solution to equilibrate for at least 24 hours;
   placing the ACF filter material into the calibration tube; and
   sealing the calibration tube.

14. The method of claim 13, wherein the salt bath solution comprises an alkali metal halide solution, potassium carbonate, magnesium nitrate, or potassium sulfate.

15. The method of claim 13, further comprising:
   breaking a portion of the calibration tube to allow air flow through the calibration tube;
   inserting the calibration tube into a first portion of a probe attached to the gas detector;
   attaching a second portion of the probe onto the first portion, wherein the second portion covers the calibration tube; and
   completing calibration of the gas detector while the calibration tube is inserted into the probe.

16. The method of claim 14, wherein the gas detector is operable to detect volatile organic compounds (VOC).

17. A calibration tube for use in calibrating a gas detector, the calibration tube comprising:
   a cylindrical glass casing defining an interior space;
   an activated carbon fiber (ACF) filter material disposed within the interior space of the cylindrical glass casing, wherein the ACF filter material is pretreated to enable the ACF filter material to maintain a humidity level greater than zero by a method comprising:
      heating the ACF filter material to 160° C. for approximately 1.5 hours;
      enclosing the ACF filter material in a glass chamber with a salt bath solution; and
      allowing the ACF filter material and the salt bath solution to equilibrate for at least 24 hours;
   a first breakable end configured to seal a first end of the cylindrical glass casing; and
   a second breakable end configured to seal a second end of the cylindrical glass casing.

18. The calibration tube of claim 17, wherein the salt bath solution comprises an alkali metal halide solution, potassium carbonate, magnesium nitrate, or potassium sulfate.

19. The calibration tube of claim 17, wherein the calibration tube is configured to be received into a calibration device, wherein the calibration device comprises:
   housing configured to attach to a main body of the gas detector and configured to hold the calibration tube during calibration;
   a cap configured to attach to the housing so as to fit over and cover the calibration tube; and
   one or more inlets configured to allow air-flow via the calibration tube when the calibration tube is received into the calibration device.

* * * * *